(12) United States Patent
Kim et al.

(10) Patent No.: US 12,274,983 B2
(45) Date of Patent: Apr. 15, 2025

(54) MEMBRANE STRUCTURE BODY HAVING MATRIX STRUCTURE AND BIOMOLECULE FILTER USING SAME

(71) Applicant: METAPORE CO., LTD, Suwon-si (KR)

(72) Inventors: Kyu Nam Kim, Suwon Si (KR); Sunghoon Kim, Suwon (KR)

(73) Assignee: Metapore Co., Ltd. (KR)

(*) Notice: Subject to any disclaimer, the term of this patent is extended or adjusted under 35 U.S.C. 154(b) by 1071 days.

(21) Appl. No.: 16/964,855

(22) PCT Filed: Jan. 25, 2019

(86) PCT No.: PCT/KR2019/001102
§ 371 (c)(1),
(2) Date: Feb. 22, 2021

(87) PCT Pub. No.: WO2019/147071
PCT Pub. Date: Aug. 1, 2019

(65) Prior Publication Data
US 2021/0162348 A1     Jun. 3, 2021

(30) Foreign Application Priority Data

Jan. 26, 2018  (KR) .......................... 1020180010006
Jan. 25, 2019  (KR) ................................ 2019001102

(51) Int. Cl.
*B01D 63/08* (2006.01)
*B01D 61/14* (2006.01)
(Continued)

(52) U.S. Cl.
CPC ......... *B01D 63/087* (2013.01); *B01D 61/147* (2013.01); *B01D 61/18* (2013.01);
(Continued)

(58) Field of Classification Search
CPC .......... B01D 2313/025; B01D 2313/08; B01D 2313/086; B01D 2313/16; B01D 61/147;
(Continued)

(56) References Cited

U.S. PATENT DOCUMENTS 5,753,014 A * 5/1998 Van Rijn ............... B01D 69/108
                                                            96/13
5,843,767 A    12/1998 Beattie
(Continued)

FOREIGN PATENT DOCUMENTS

CN         102639215 A     8/2012
EP           0879635 A1   11/1998
(Continued)

OTHER PUBLICATIONS 201980008646.5 Chinese Office Action, dated Sep. 28, 2021, 8 pages.
(Continued)

*Primary Examiner* — Jennifer Wecker
*Assistant Examiner* — Jonathan Bortoli
(74) *Attorney, Agent, or Firm* — Nolte Lackenbach Siegel; Myron Greenspan

(57) ABSTRACT

A membrane structure body having a matrix structure and a biomolecule filter using the same are disclosed. The membrane structure body having a matrix structure, according to one embodiment of the present disclosure, comprises: a filtering part which includes a window region in which a plurality of window cells are formed in a matrix shape and a blocking region in which the window cells are not formed, and which filters biomolecules from a sample moving along the window region; and a support part extending from the filtering part so as to support the filtering part, wherein each of the window cells formed in the window region of the filtering part has have micro-holes allowing the biomol-
(Continued)

ecules having a predetermined size or less to pass therethrough.

12 Claims, 4 Drawing Sheets

(51) Int. Cl.
    *B01D 61/18* (2006.01)
    *G01N 1/34* (2006.01)
    *G01N 1/40* (2006.01)
(52) U.S. Cl.
    CPC ............ *G01N 1/34* (2013.01); *G01N 1/4077* (2013.01); *B01D 2313/086* (2013.01); *B01D 2313/16* (2013.01); *G01N 2001/4088* (2013.01)
(58) Field of Classification Search
    CPC .... B01D 61/18; B01D 63/087; B01D 63/088; B01D 69/00; B01D 71/0215; C12N 15/1017; G01N 1/34; G01N 1/4077; G01N 2001/4088; C12Q 1/6806
    See application file for complete search history.

(56) References Cited

U.S. PATENT DOCUMENTS

| | | | |
|---|---|---|---|
| 9,403,126 B2 | 8/2016 | Fissell et al. | |
| 9,638,636 B2 | 5/2017 | Tibbe et al. | |
| 2004/0149688 A1 | 8/2004 | Fuchs et al. | |
| 2004/0245102 A1* | 12/2004 | Gilbert | B01L 3/502715 156/60 |
| 2008/0200343 A1* | 8/2008 | Clemens | G01N 27/27 506/13 |
| 2009/0148933 A1* | 6/2009 | Battrell | C12Q 1/686 435/287.2 |
| 2013/0004898 A1* | 1/2013 | Wang | B81C 1/0038 427/535 |
| 2014/0190903 A1* | 7/2014 | Huang | B01L 3/502753 210/323.1 |
| 2015/0160135 A1 | 6/2015 | Tibbe et al. | |

FOREIGN PATENT DOCUMENTS

| | | |
|---|---|---|
| EP | 2506956 B1 | 8/2012 |
| JP | 09504864 | 5/1997 |
| JP | 2008540070 A | 11/2008 |
| KR | 1020050065895 | 6/2005 |
| KR | 100934267 | 12/2009 |
| KR | 1020140117944 | 10/2014 |
| WO | 2011068753 | 6/2011 |
| WO | 2019147071 | 8/2019 |

OTHER PUBLICATIONS 201980008646.5 Chinese Office Action, dated Mar. 16, 2022, 9 pages.
201980008646.5 Chinese Office Action, dated Jul. 19, 2022, 7 pages.
201980008646.5 Chinese Office Action, dated Oct. 19, 2022, 7 pages.
EP 19743513 Supplementary EP Search Report, dated Oct. 18, 2021, 9 pages.
Earhart et al., Mircofabricated Magnetic Sifter for High-Throughput and High-Gradient Magnetic Separation, Journal of Magnetism and Magnetic Materials 321 (2009) pp. 1436-1439.
2020-561565 Japanese Office Action, 3 pages.

* cited by examiner

MEMBRANE STRUCTURE BODY HAVING MATRIX STRUCTURE AND BIOMOLECULE FILTER USING SAME

FIELD OF THE DISCLOSURE

The present disclosure relates to a membrane structure having a biomolecule filter and a biomolecule filter using the same, and more specifically, to a membrane structure having a plurality of window cells arranged in a matrix shape and a biomolecule filter for filtering biomolecules included in a sample using the same.

RELATED ART

The present disclosure claims priority to Korean Patent Application No. 10-2018-0010006 filed on Jan. 26, 2018, and the entire specification is a reference of the present disclosure.

In general, a biomolecule refers to a substance constituting a living body (e.g., nucleic acids, proteins, microvesicles, etc.) or a substance derived from a living body. Recently, as it is known that diseases such as cancer and Alzheimer's disease can be diagnosed using exosomes (i.e., signaling substances between cells), interests and studies are rapidly increasing with respect to technologies for efficient separation of specific biomolecules (e.g., exosomes).

However, the existing technology for separating vesicles in body fluids by fixing antibodies, which bind to vesicle proteins to microchip, requires that a centrifugation process be performed as a pretreatment process and that expensive equipment be used for the fixation of antibodies. Therefore, there were problems in that biomolecules may be damaged and much time and cost are required for the separation of biomolecules.

Additionally, as disclosed in Korean Patent Application Publication No. 10-0550515, the existing technology for separating biomolecules using a porous membrane employs a simple film type dry film resist (DFR) film or polycarbonate film, there is a problem in that the porous membrane has poor durability and it is difficult to handle and install the porous membrane. Moreover, according to the existing technology, biomaterials are filtered in a static state where a sample is filled into channel on which a porous membrane is installed, there is a problem in that a porous membrane is blocked by other substances included in the sample, thus rapidly deteriorating its filtering efficiency.

SUMMARY OF THE DISCLOSURE

A technical problem to solve in the present disclosure is to provide a membrane structure having a matrix structure, which in the process of separating biomolecules included in a sample, not only prevents damage to a biomolecule and saves time and money, but also improves the durability of a membrane structure and prevents blockage of the membrane structure by substances other than biomolecules to be filtered and subsequent deterioration in its filtering efficiency; and a biomolecule filter using the same.

A membrane structure having a matrix structure according to an embodiment of the present disclosure includes a filtering part, which includes a window region in which a plurality of window cells are formed in a matrix shape; and a blocking region in which the window cells are not formed, and which filters biomolecules from a sample moving along the window region; and a support part, which extends from the filtering part so as to support the filtering part, wherein each of the window cells formed in the window region of the filtering part is configured to have micro-holes allowing the biomolecules having a predetermined size or less to pass therethrough, and thus filters biomolecules included in the sample.

In an embodiment, the filtering part may include a plurality of window regions, and the plurality of window regions be configured to be placed side by side by being spaced apart one after the other with the blocking region placed therebetween.

In an embodiment, the membrane structure the membrane structure may have a matrix structure with a laminated structure, which includes a substrate on which through holes constituting the window cells are formed; and a porous membrane which is laminated on the substrate and covers one side opening of the through holes.

In an embodiment, the substrate may include a silicon substrate.

In an embodiment, the substrate may further include a silicon oxide ($SiO_2$) layer laminated on the silicon substrate.

In an embodiment, the porous membrane may consist of silicon nitride ($Si_3N_4$).

A biomolecule filter according to an embodiment of the present disclosure is a filter for filtering biomolecules included in a sample using the membrane structure according to any of the embodiments described above, which includes a first housing, which is located on a side of one surface of the membrane structure and receives a sample and transports the sample along the window region of the membrane structure; and a second housing, which is located on a side of the other surface of the membrane structure and collects biomolecules coming out through the other surface of the membrane structure.

In an embodiment, the first housing may include an inlet, through which the sample is flowed in; a first outlet, which discharges a remaining sample from which at least some of the biomolecules are separated; and a first flow path, which transports the sample flowed in through the inlet along the window region of the membrane structure and then delivers the sample to the first outlet.

In an embodiment, the first flow path may include a flow path groove, which is formed along the window region of the membrane structure and connects the inlet and the first outlet; and a diaphragm, which is formed around the flow path groove and prevents leakage of a sample.

In an embodiment, the first housing may further include a first adhesive part to which an adhesive is applied, which is adhered to a support part of the membrane structure; and a first vent hole, which allows the first adhesive part to communicate with the outside of the first housing.

In an embodiment, the second housing may include a second outlet, which discharges biomolecules separated through the membrane structure; and a second flow path, which transports biomolecules coming out through the other surface of the membrane structure and delivers the biomolecules to the second outlet.

In an embodiment, the second flow path may include a second flow path groove, which includes a plurality of guide grooves that are configured to extend side by side at mutually spaced intervals to guide the movement of the biomolecules coming out from the other surface of the membrane structure in a certain direction; a collecting groove, which collects the biomolecules guided and moved by the plurality of guide grooves and delivers the biomolecules to the second outlet; and a second diaphragm, which is formed around the second flow path groove and prevents leakage of biomolecules.

In an embodiment, the second housing may further include a second adhesive part to which an adhesive is applied, which is adhered to a support part of the membrane structure; and a second vent hole, which allows the second adhesive part to communicate with the outside of the second housing.

DESCRIPTION OF EXEMPLARY EMBODIMENTS

Hereinafter, embodiments of the present disclosure will be described in detail with reference to the accompanying drawings in order to clarify solutions to the technical problems of the present disclosure. However, in explaining the present disclosure, a description of related publicly known technology will be omitted if it makes the gist of the present disclosure unclear. In addition, the terms to be described later are terms defined in consideration of functions in the present disclosure, which may vary according to intentions or practices of a designer, a manufacturer, etc. Therefore, the definition should be made based on the contents throughout this specification.

In the present specification, the term "biomolecule" refers to not only a substance constituting a living body (nucleic acids, proteins, microvesicles, etc.) and a substance derived from a living body, but also all the substances formed by binding, decomposition, modification, or mutation of these substances.

Figure 1:
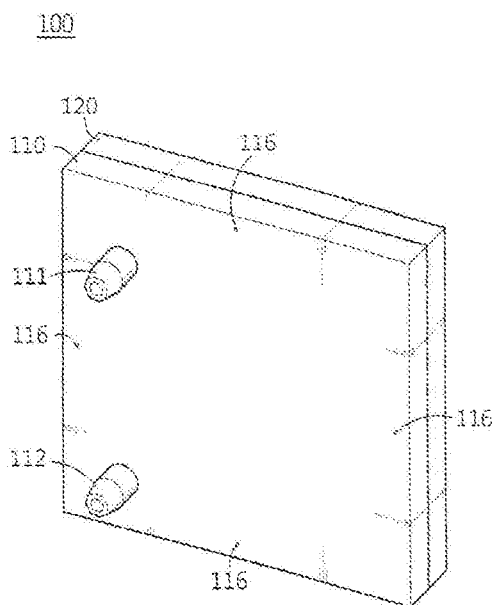
FIG. 1 is a front perspective view showing a biomolecule filter according to an embodiment of the present disclosure.

FIG. 1 shows the biomolecule filter 100 according to an embodiment of the present disclosure is shown in a front perspective view.

As shown in FIG. 1, the biomolecule filter 100 according to an embodiment of the present disclosure may include a first housing 110, a second housing 120, and a membrane structure (not shown) installed between the first housing 110 and the second housing 120.

The first housing 110 is located on a side of one surface of a membrane structure and is configured to receive a sample and bring the sample into contact with the membrane structure. For this purpose, the first housing 110 may include a first outlet 111, an inlet 112, and a first flow path (not shown).

The inlet 112 is configured such that a sample being supplied from the outside of the first housing 110 flows into the inside of the first housing 110. For example, the inlet 112 may be configured to include a protrusion for inserting a sample supply pipe formed on an outer surface of the first housing 110, and a through hole extending from an end of the protrusion to an inner surface of the first housing 110.

The first outlet 111 is configured to discharge a remaining sample, in which at least some the biomolecules are separated from the sample flowed into the inlet 112. For example, the first outlet 111 may be configured to include a protrusion for inserting a sample collection tube formed on the outer surface of a first housing 110 and a through hole extending from the inner surface of the first housing 110 to the distal end of the sample collection tube.

As will be described again below, a first flow path of the first housing 110 transports the sample flowed in through the inlet 112 along a certain pathway on one surface thereof while bringing the sample into contact with one surface of the membrane structure, and delivers the sample to the first outlet 111.

Additionally, the first housing 110 may further include a first vent hole 116 which allows the inside of the first housing 110 to communicate with the outside of the first housing 110.

Figure 2:
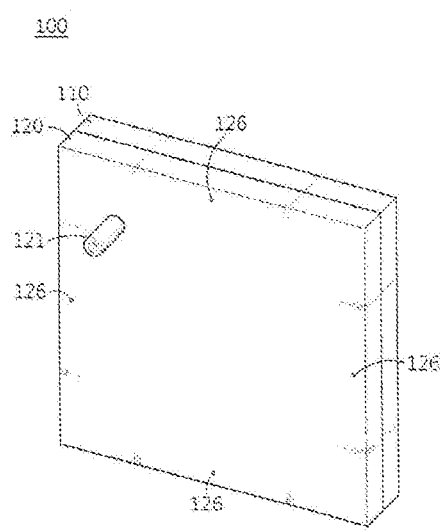
FIG. 2 is a rear perspective view showing the biomolecule filter shown in FIG. 1.

FIG. 2 shows the biomolecule filter 100 shown in FIG. 1 in a rear perspective view.

As shown in FIG. 2, the second housing 120 of the biomolecule filter 100 according to an embodiment of the present disclosure is located on a side of the other surface of the membrane structure corresponding to a first housing 110 and is configured to collect and discharge biomolecules coming out through the other surface of the membrane structure. For this purpose, the second housing 120 may include a second outlet 121 and a second flow path (not shown).

The second outlet 121 is configured to discharge biomolecules separated through the membrane structure. For example, the second outlet 121 may be configured to include a protrusion for inserting biomolecule collection tube formed on an outer surface of the second housing 120 and a through hole extending from an inner surface of the second housing 120 to a distal end of the protrusion for inserting the biomolecule collection tube.

As will be described again below, the second flow path of the second housing 120 is configured to collect biomolecules coming out through the other surface of the membrane structure and deliver the biomolecules to the second outlet.

Additionally, the second housing 120 may further include a second vent hole 126 which allows the inside of the second housing 120 to communicate with the outside of the second housing 120.

Figure 3:
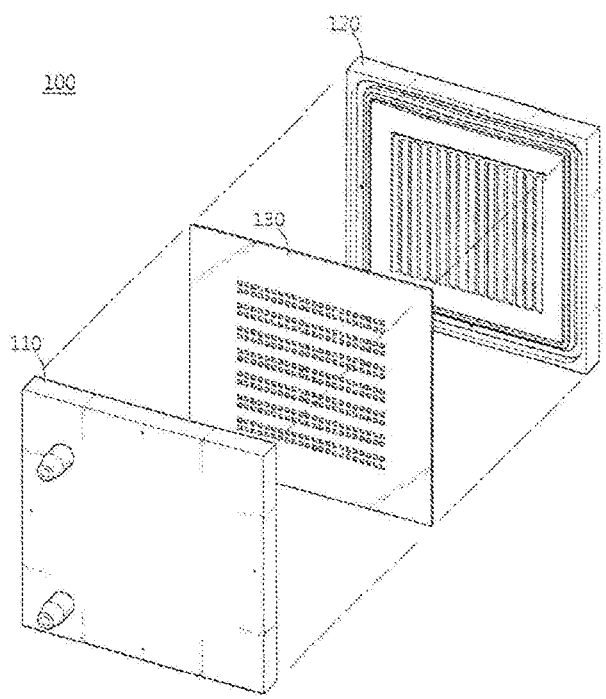
FIG. 3 is an exploded perspective view showing the biomolecule filter shown in FIG. 1.

FIG. 3 shows the biomolecule filter 100 shown in FIG. 1 in an exploded perspective view.

As shown in FIG. 3, the biomolecule filter 100 includes a membrane structure 130 and filters biomolecules included in a sample using the membrane structure 130. That is, the first housing 110 is located on a side of one surface of the membrane structure 130 and is coupled to one surface of the membrane structure 130, and the second housing 120 is located on a side of the other surface of the membrane structure 130 and is coupled to the other surface of the membrane structure 130. According to an embodiment, the first housing 110 and the second housing 120 may be configured to accommodate the membrane structure 130. For example, the first housing 110 and the second housing 120 may accommodate the membrane structure 130 in the inner space formed by a mutual binding, and as described above, the first housing 110 may be coupled to one surface of the membrane structure 130, and the second housing 120 may be coupled to the other surface of the membrane structure 130.

Figure 4:
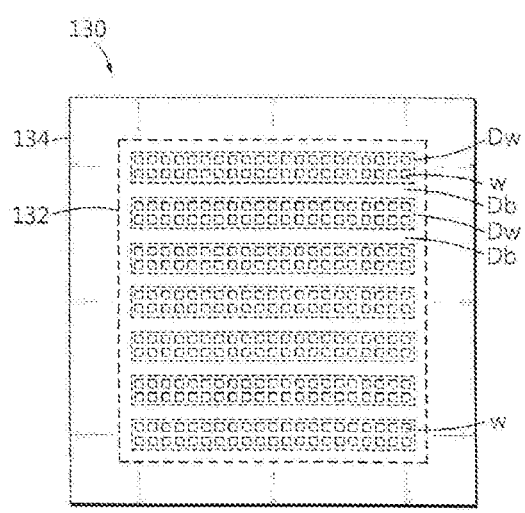
FIG. 4 is a plan view showing a membrane structure having a matrix structure according to an embodiment of the present disclosure.

FIG. 4 shows the membrane structure 130 having a matrix structure according to an embodiment of the present disclosure in a plan view.

As shown in FIG. 4, the membrane structure 130 according to an embodiment of the present disclosure is a membrane-shaped structure configured to filter biomolecules included in a sample, and it includes a filtering part 132 and a support part 134.

The filtering part 132 is a part in which filtering of biomolecules is performed, and it includes a window region (Dw), where the window cells (w) are formed, and a blocking region (Db) where the window cells (w) are not formed.

The window region (Dw) of the filtering part 132 is a region in which a plurality of window cells (w) are configured to be formed in a matrix form along the moving path of a sample so as to contact the sample. The first housing 110 being coupled to the membrane structure 130 forms a flow path along the window region (Dw) of the filtering part 132 and transports the sample through the corresponding flow path. The filtering part 132, as described above, filters biomolecules from the sample moving along the window region (Dw). For this purpose, each of the window cells (w) formed in the window region (Dw) has a plurality of micro-holes allowing the biomolecules having a predetermined size or less to pass therethrough.

The blocking region (Db) of the filtering part 132 is a region excluding the window region (Dw) among the entire regions of the filtering part 132, where the filtering of biomolecules does not occur. In the blocking region (Db), a diaphragm of the first housing 110, which will be described later, is located, thereby preventing leakage of a sample moving along the window region (Dw).

According to an embodiment, the filtering part 132 may include a plurality of window regions (Dw) as shown in FIG. 4. In this case, the plurality of window regions (Dw) may be arranged side by side with the blocking region (Db) placed therebetween.

Meanwhile, the support part 134 is configured to extended or enlarged from the filtering part 132 so as to support the filtering part 132. That is, the support part 134 is a part corresponding to a frame that supports a filtering part 132, by being gripped by a user when transporting the membrane structure 100 or being adhered or inserted into another structure when the membrane structure 100 is installed.

When a membrane structure 130 is configured in the form of a square plate as shown in FIG. 4, the filtering part 132 may be located at the central portion of the membrane structure 130, and the support part 134 may be located at the edge portion of the membrane structure 130. The shape and size of the membrane structure 130, the locations of the filtering part 132 and the support part 134, etc. can be variously changed according to the environment to which the membrane structure 100 is applied.

One thing to be noted in the present disclosure is that the biomolecules included in the sample to be filtered are not separated by window cells (w) formed in the window region (Dw), but they are separated by micro-holes in each window cell (w). That is, the size and shape of the window cell are independent of the size of the biomolecules to be filtered.

Figure 5:
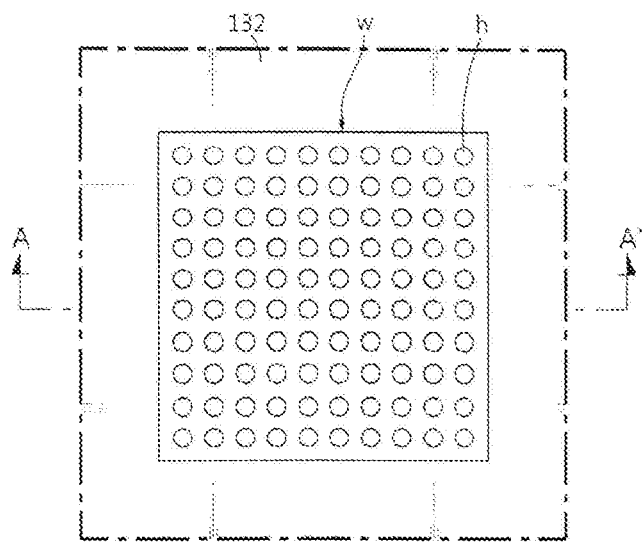
FIG. 5 is an enlarged view showing a window cell portion of the membrane structure shown in FIG. 4.

FIG. 5 shows an enlarged view of the window cell (w) portion of the membrane structure 130 shown in FIG. 4

As shown in FIG. 5, a plurality of fine holes (h) are formed in each window cell (w) formed in the filtering part 132 of the membrane structure 130. The size of the window cell (w) may be configured, for example, as a 1.2 mm×1.2 mm size when the membrane structure 130 is composed of a 50 mm×50 mm size. That is, the size and shape of the window cell (w) are independent of the size of biomolecules to be filtered, and can be variously changed according to the strength, thickness, etc. of the window cell structure.

Meanwhile, the size of the micro-holes (h) formed in the window cell (w) is determined according to the size of biomolecules to be filtered. That is, the micro-holes (h) formed in the window cell (w) may be configured to have a diameter corresponding to a range between 10 nm or more and 300 nm or less. For example, when the biomolecules to be filtered are exosomes, a plurality of micro-holes (h) formed in the window cell (w) may be configured to have a diameter corresponding to a range between 10 nm or more and 300 nm or less.

Figure 6:
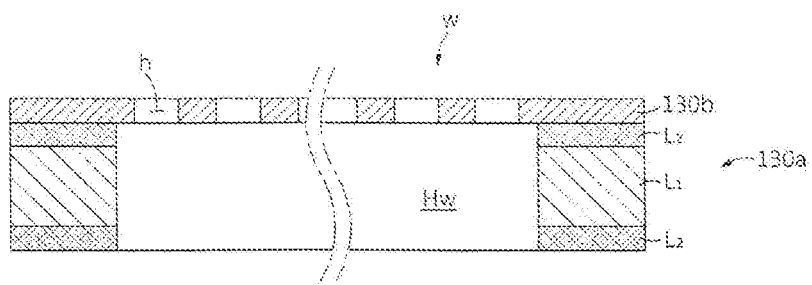
FIG. 6 is a vertical cross-sectional view showing part A-A' shown in FIG. 5.

FIG. 6 shows a part A-A' shown in FIG. 5 in a vertical sectional view.

As shown in FIG. 6, the membrane structure 130 may have a laminated structure including a substrate 130a and a porous membrane 130b.

The substrate 130a corresponds to the basic frame of the membrane structure 130 and it may include a silicon substrate L1 that establishes a core layer. Additionally, the substrate 130a may further include a silicon oxide layer (L2) laminated on the silicon substrate L1 to prevent deformation or cracking of the substrate due to residual stress. The silicon oxide layer L2 may be laminated on both the upper and lower surfaces of the silicon substrate L1 as shown in FIG. 6, and it may be laminated on only one of the upper and lower surfaces according to an embodiment. In an embodiment, the silicon oxide layer L2 may be laminated on the silicon a substrate L1 through a deposition process of a semiconductor manufacturing technology.

Through holes (Hw) for forming the window cell (w) are formed in such a substrate 130a. In this case, the through holes (Hw) may be formed through a lithography process of a semiconductor manufacturing technology.

The porous membrane 130b, which corresponds to the porous structure of the window cell (w), is supported by being laminated on one surface of the substrate 130a with a plurality of micro-holes (h) passing biomolecules of a certain size or less, and it covers one side opening of the through hole (Hw)

In an embodiment, the porous membrane 130b may be composed of a silicon-based compound. For example, the porous membrane (130b) may be composed of at least one compound selected from the group consisting of silicon nitride ($Si_3N_4$), silicon oxide (SiO 2), and silicon carbide (SiC), and in particular silicon nitride ($Si_3N_4$).

Silicon nitride is a material mainly used as a passivation film to prevent alkali ions from diffusing into the semiconductor surface during the manufacture of semiconductors. In the present disclosure, considering the characteristics of silicon nitride (i.e., high strength (bending strength of 100-140 kg/mm$^2$ at room temperature), low thermal expansion rate (thermal expansion rate: $3\times10^{-6}/°$ C.), and excellent heat shock resistance), silicon nitride is selected as a substance for the porous membrane 130b.

In this case, the porous membrane 130b may be configured to have a nano-sized thickness, that is, a thickness corresponding to a range between 50 nm or more and 500 nm or less. When the thickness of the porous membrane 130b is less than 50 nm, the strength of the porous membrane 130b decreases and is likely to be broken during the process of manufacture or use. In contrast, when the thickness of the porous membrane 130b is greater than 500 nm, the time required for the separation of biomolecules becomes longer and the separation efficiency decreases. In order to simultaneously satisfy the membrane strength and the separation efficiency of biomolecules, the porous membrane 130b may be configured to have a thickness corresponding to a range between 100 nm or more and 300 nm or less.

Meanwhile, the size of the micro-holes (h) formed in the porous membrane 130b is determined according to the size of the biomolecules to be filtered. That is, the plurality of the micro-holes (h) formed in the porous membrane 130b may be configured to have a diameter corresponding to a range between 10 nm or more and 3,000 nm or less. For example, when the biomolecules to be filtered are exosomes, a plurality of micro-holes (h) formed in the porous membrane 130b may be configured to have a diameter corresponding to a range between 10 nm or more and 300 nm or less. In this case, the nano-sized micro-holes formed on the porous membrane 130b may be formed through electron beam lithography or X-ray lithography process with high resolution.

Figure 7:
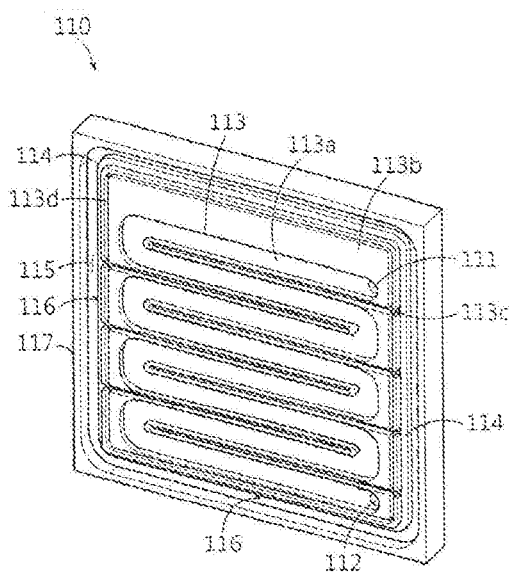
FIG. 7 is a perspective view showing the inner surface of the first housing shown in FIG. 3.

FIG. 7 shows the inner surface of the first housing 110 shown in FIG. 3 in a perspective view.

As shown in FIG. 7, the first housing 110 is located on a side of one surface of the membrane structure 130 and is configured to receive a sample including biomolecules to be filtered and transports the sample along the window region (Dw) of the membrane structure 130. For this purpose, the first housing 110 includes a first outlet 111, an inlet 112, and a first flow path 113, and according to an embodiment, it may further include a first vent hole 116, a first outer diaphragm 117, etc.

As mentioned above, the inlet 112 is configured such that the sample including biomolecules to be filtered flows in from the outside of the first housing 110 to the inside. Additionally, the first outlet 111 is configured to discharge a remaining sample, in which at least some of the biomolecules are separated from the sample flowed in through the inlet 112.

The first flow path 113, which connects the inlet 112 and the first outlet 111, is configured to transport the sample flowed in through the inlet 112 along the window region (Dw) while bringing the sample into contact with the window region (Dw) of the membrane structure 130, and then delivers the sample to the first outlet 111. In this case, the first flow path 113 may be configured to deliver the entire sample flowed therein to the first outlet 111 after bringing the sample into contact with a plurality of window regions (Dw) of the membrane structure 130.

For example, the first flow path 113 may be configured to form, on one surface of the membrane structure 130, a moving path of the sample in the form of a meander that connects the inlet 112 and the first outlet 111. In this case, the first flow path 113 be configured such that it transports the sample flowed in through the inlet 112 along the window region of the membrane structure 130 in a zigzag direction as shown in FIG. 7 and gradually advances the sample to a side of the first outlet 111.

Additionally, the first flow path 113 may include the first flow path groove 113a and the first inner diaphragm 113b. The first flow path groove 113a is a groove structure connecting the inlet 112 and the first outlet 111, and it may be configured in a meander form as described above. The first inner diaphragm 113b is formed around the first flow path groove 113a and it may be configured to prevent leakage of a sample from the first flow path groove 113a.

In an embodiment, the first housing 110 may further include a sealing member (not shown) that seals between one surface of the membrane structure 130 and the first inner diaphragm 113b of the first flow path 113. Such a sealing member may be composed of a polymer synthetic resin having adhesiveness and water resistance. According to an embodiment, the sealing member may include a rubber member which comes in close contact with one surface of the membrane structure 130. In this case, the first inner diaphragm 113b may include an installation groove 113c into which the rubber member is inserted to be installed.

Additionally, in an embodiment, the first inner diaphragm 113b may further include a first adhesive blocking groove 113d which is formed between the first flow path groove 113a and the first adhesive part 114 described below. The first adhesive blocking groove 113d is configured to receive the remaining amount of the adhesive flowing out of the corresponding adhesive surface during an adhesion between the first adhesive part 114 and the membrane structure 130, so that the adhesive can be prevented from flowing into the first flow path groove 113a.

Meanwhile, the first adhesive part 114 is a part to which an adhesive is applied, and it is adhered to one surface of the membrane structure 130. In this case, the first adhesive part 114 has a height difference with the first inner diaphragm 113b of the first flow path 113 in consideration of the thickness of the adhesive layer being formed by the adhesive and it may be formed to be lower than the first inner diaphragm 113b. Additionally, the first adhesive part 114 may be configured as an annular structure to be adhered to the support part 134 corresponding to the edge portion of the membrane structure 130.

The first adhesive receiving groove 115 is a groove formed around the outer periphery of the first adhesive part 114, and basically, an adhesive may be applied as in the first adhesive part 114. In this case, the first adhesive receiving groove 115 may be configured to receive a remaining amount of the adhesive flowing out of the corresponding adhesive surface during an adhesion between the first adhesive part 114 and the membrane structure 130 and to be adhered to the membrane structure 130. When the first adhesive part 114 is configured in an annular structure, the first adhesive receiving groove 115 may be configured to be formed as an annular groove formed along the first adhesive part 114.

The first vent hole 116 is configured to allow the first adhesive part 114 to communicate with the outside of the first housing 110. The first vent hole 116 can discharge the gas generated during an adhesion between the first adhesive part 114 and the membrane structure 130 or a remaining amount of adhesive thereof to the outside. In this case, the first vent hole 116 may be formed in the first adhesive receiving groove 115.

The first outer diaphragm 117, which is the outermost structure of the first housing 110, is configured to protect the membrane structure 130 by preventing external exposure of the membrane structure 130. For example, the first outer diaphragm 117 may be configured to adhere to the outermost edge portion of the membrane structure 130. In this case, the first outer diaphragm 117 may be adhered to the membrane structure 130 by the adhesive being flowed therein in the process of the adhesion of the first adhesive part 114 and the first adhesive receiving groove 115 with the membrane structure 130, even when an adhesive is not applied in advance as is the case with the first adhesive part 114 or the first adhesive receiving groove 115.

Figure 8:
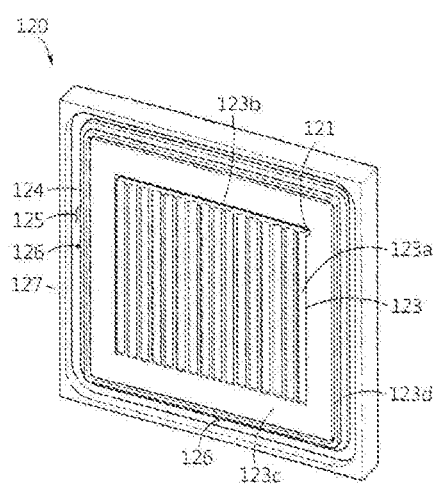
FIG. 8 is a perspective view showing the inner surface of the second housing shown in FIG. 3

FIG. 8 shows the inner surface of the second housing 120 shown in FIG. 3 in a perspective view.

As shown in FIG. 8, the second housing 120 is located on a side of the other surface of the membrane structure 130 corresponding to the first housing 110 located on a side of one surface of the membrane structure 130, and is configured to collect and discharge biomolecules coming out through the other side of the membrane structure 130. For this purpose, the second housing 120 includes the second outlet 121 and the second flow path 123, and according to an embodiment, may further include a second adhesive part 124, a second adhesive receiving groove 125, a second vent hole 126, a second diaphragm 127, etc.

As mentioned above, the second outlet 121 is configured to discharge the biomolecules separated through the membrane structure 130.

The second flow path 123 is configured to transport the biomolecules coming out through the micro-holes of each window cell (w) on the other surface of the membrane structure 130 and deliver them to the second outlet 121. For this purpose, the second flow path 123 may include the second flow path grooves (123a and 123b) and a second diaphragm 123c.

The second flow path grooves (123a, 123b) are of groove structures which connect the other surface of the membrane structure 130 and the second outlet 121, and they may include a plurality of guide grooves 123a and collection grooves 123b.

The plurality of guide grooves 123a are grooves for guiding the movement of the biomolecules coming out through each window cell (w) from the other surface of the membrane structure 130 in a certain direction (i.e., in a direction of the collection groove 123b), and they may be composed of elongated grooves extending side by side at regular intervals so as to cover at least the region corresponding to the filtering part 132 of the entire region of the membrane structure 130.

The collection groove 123b is a groove which is guided by the plurality of guide grooves 123a and collects and delivers biomolecules to the second outlet 121, and the collection groove 123b may be configured to connect each guide groove 123a with the second outlet 121.

The second diaphragm 123c may be configured to to be formed around the second flow path grooves (123a, 123b) so as to prevent leakage of biomolecules.

In an embodiment, the second housing 120 may further include a sealing member (not shown) for sealing between the other surface of the membrane structure 130 and the second diaphragm 123c. Such a sealing member may be composed of a polymer synthetic resin having adhesiveness and water resistance.

Additionally, in an embodiment, the second diaphragm 123c may further include a second adhesive blocking groove 123d formed between the second flow path grooves (123a, 123b) and the second adhesive part 124 to be described later. The second adhesive blocking groove 123d may be configured to receive the remaining amount of the adhesive flowing out of the corresponding adhesive surface during an adhesion between the second adhesive part 124 and the membrane structure 130, and thereby block the adhesive from flowing into the second flow path grooves (123a, 123b).

Meanwhile, the second adhesive part 124 is a portion to which an adhesive is applied, and it is adhered to the other surface of the membrane structure 130. In this case, the second adhesive part 124 has a height difference with the second diaphragm 123c of the second flow path 123 in consideration of the thickness of the adhesive layer being formed by the adhesive and it may be formed to be lower than the second diaphragm 123c. Additionally, the second adhesive part 124 may be configured in an annular structure to be adhered to the support part 134 corresponding to the edge portion of the membrane structure 130.

The second adhesive receiving groove 125 is a groove formed around the outer periphery of the second adhesive part 124, and basically, an adhesive may be applied as in the second adhesive part 124. In this case, the second adhesive receiving groove 125 may be configured to receive a remaining amount of the adhesive flowing out of the corresponding adhesive surface during an adhesion between the second adhesive part 124 and the membrane structure 130 and to be adhered to the membrane structure 130. When the second adhesive part 124 is configured in an annular structure, the second adhesive receiving groove 125 may be configured to be formed as an annular groove formed along the second adhesive part 124.

The second vent hole 126 is configured to allow the second adhesive part 124 to communicate with the outside of the second housing 120. The second vent hole 126 can discharge the gas generated during an adhesion between the second adhesive part 124 and the membrane structure 130 or a remaining amount of adhesive thereof to the outside. In this case, the second vent hole 126 may be formed in the second adhesive receiving groove 125.

The second diaphragm 127, which is the outermost structure of the second housing 120, is configured to protect the membrane structure 130 by preventing external exposure of the membrane structure 130. For this purpose, the second diaphragm 127 may be configured to adhere to the outermost edge portion of the membrane structure 130. In this case, the second diaphragm 127 may be adhered to the membrane structure 130 by the adhesive being flowed therein in the process of the adhesion of the second adhesive part 124 and the second adhesive receiving groove 125 with the membrane structure 130, even when an adhesive is not applied in advance as is the case with the second adhesive part 124 or the second adhesive receiving groove 125.

The biomolecule filter 100 configured as such can discharge the remaining sample, in which some of the biomolecules are separated, to the first outlet 111 of the first housing 110, while discharging the filtered biomolecules to the second outlet 121 of the second housing 120, after filtering the biomolecules included in the sample supplied through the inlet 112 of the first housing 110 while transporting the sample along the window region (Dw) of the membrane structure 130. Additionally, the biomolecule filter 100 can filter the biomolecules included in the sample by repeatedly cycling a certain amount of the sample along the window region (Dw) of the membrane structure 130 in such a manner that the remaining sample discharged through the first outlet 111 is received again through the inlet 112.

As described above, according to the present disclosure, it is possible to prevent damage to biomolecules and reduce the time and cost required for a biomolecule separation process by separating the biomolecules included in the sample via filtration through a membrane structure with a porous structure.

In particular, it is possible to improve the durability of a membrane structure and facilitates easy handling and installation of the membrane structure by forming a plurality of window cells on the membrane structure and by constructing the fragile porous structure via divisions into each window cell unit.

Additionally, as window cells filter the biomolecules included in a sample while transporting the sample along the window region of a membrane structure arranged in a matrix form, the blockage of the membrane structure caused by substances other than the biomolecules to be filtered and the subsequent deterioration in filtering efficiency can be prevented.

Additionally, the yield of biomolecules can be improved while reducing the amount of a sample required for acquiring the biomolecules, by repeatedly cycling a certain amount of the sample along the window region of a membrane structure and filtering the biomolecules contained in the sample.

Further, the embodiments according to the present disclosure can solve various technical problems other than those mentioned in the present specification in related technical fields as well as in the present technical field.

Thus far, the present disclosure has been described with reference to specific embodiments. However, those skilled in the art will clearly understand that various modified embodiments can be implemented in the technical scope of the present disclosure. Therefore, the embodiments disclosed above should be considered from an explanatory point of view rather than a limited point of view. That is, the scope of the true technical idea of the present disclosure is indicated in the claims, and all the differences within the scope of the present disclosure should be interpreted as being included in the present disclosure.

Effects of the Invention

According to the present disclosure, it is possible to prevent damage to biomolecules and reduce the time and cost required for a biomolecule separation process by separating the biomolecules included in the sample via filtration through a membrane structure with a porous structure.

In particular, it is possible to improve the durability of a membrane structure and facilitates easy handling and installation of the membrane structure by forming a plurality of window cells on the membrane structure and by constructing the fragile porous structure via divisions into each window cell unit.

Additionally, as window cells filter the biomolecules included in a sample while transporting the sample along the window region of a membrane structure arranged in a matrix form, the blockage of the membrane structure caused by substances other than the biomolecules to be filtered and the subsequent deterioration in filtering efficiency can be prevented.

Additionally, the yield of biomolecules can be improved while reducing the amount of a sample required for acquiring the biomolecules, by repeatedly cycling a certain amount of the sample along the window region of a membrane structure and filtering the biomolecules contained in the sample.

Further, any one with ordinary skill in the art to which the present disclosure belongs will clearly understand from the following description that various embodiments according to the present disclosure can solve various technical problems not mentioned above.

100 BIOMOLECULE FILTER 110: A FIRST HOUSING
111 The first outlet has a first outlet (112) and an outlet (112)
113 FIRST FLOW PATH 114: A FIRST ADHESIVE PART
115 FIRST ADHESIVE RECEIVING GROOVE 116: FIRST VENT HOLE
117 OUTER WALL PART 120: SECOND HOUSING
121 SECOND OUTLET 123: SECOND FLOW PATH
124 The second adhesive part 125: the second adhesive receiving groove
126 The second vent hole 127: the second outer wall part
130 MEMBRANE STRUCTURE 132: A FILTERING UNIT
134 SUPPORT

What is claimed is:

1. A membrane structure for filtering a sample comprising a plurality of biomolecules of varying sizes, the membrane structure comprising:
a filtering part having a first surface and a second surface opposite to the first surface the filtering part comprising a plurality of window regions spaced apart by a blocking region interposing each window region of the plurality of window regions, each window region of the plurality of window regions having a plurality of window cells arranged in a matrix configuration defining a flow path along the first surface, the flow path including a flow path end, each window region having a plurality of micro-holes, each micro-hole of the plurality of micro-holes having a substantially equal predetermined size, the plurality of window regions being configured to enable biomolecules within the sample having up to a predetermined size to pass from the first surface to the second surface and to retain biomolecules having a size larger than the predetermined size on the first surface as the sample flows along said flow path thereby enabling a size-based separation of biomolecules along the plurality of window regions; and
a support part extending from the filtering part so as to support the filtering part; and
a membrane structure outlet disposed at the flow path end and configured to receive the biomolecules having up to the predetermined size.

2. The membrane structure of claim 1, wherein the membrane structure has a matrix structure having a laminated structure, comprising:
a substrate on which through holes constituting the plurality of window cells are disposed; and
a porous membrane laminated on the substrate and covering an opening of the through holes on a side of the substrate.

3. The membrane structure of claim 2, wherein the substrate comprises a silicon substrate.

4. The membrane structure of claim 3, wherein the substrate further comprises a silicon oxide (SiO2) layer laminated on the silicon substrate.

5. The membrane structure of claim 2, wherein the porous membrane consists of silicon nitride (Si3N4).

6. A biomolecule filter for filtering biomolecules included in a sample, the biomolecule filter comprising the membrane structure according to claim 1, the biomolecule filter comprising:
a first housing located at said first surface of the membrane structure and configured to receive a sample and to transport the sample along the plurality of window regions of the membrane structure; and
a second housing located at said second surface of the membrane structure and configured to collect biomolecules coming out through said second surface of the membrane structure.

7. The biomolecule filter of claim 6, wherein the first housing comprises: an inlet for introducing the sample;
a first outlet configured to discharge a remaining sample from which at least some of the biomolecules are separated; and a first flow path configured to transport the sample introduced through the inlet along the plurality of window regions of the membrane structure and to deliver the sample to the first outlet.

8. The biomolecule filter of claim 7, wherein the first flow path comprises:
   a flow path groove disposed along the plurality of window regions of the membrane structure and connecting the inlet and the first outlet; and
   a diaphragm disposed around the flow path groove and configured to prevent a leakage of a sample.

9. The biomolecule filter of claim 7, wherein the first housing further comprises:
   a first adhesive part including an adhesive adhered to the support part of the membrane structure; and
   a first vent hole enabling the first adhesive part to communicate with an exterior of the first housing.

10. The biomolecule filter of claim 6, wherein the second housing comprises:
    a second outlet configured to discharge biomolecules separated through the membrane structure; and
    a second flow path configured to transport biomolecules coming out through said second surface of the membrane structure and to deliver the biomolecules coming out through said second surface of the membrane structure to the second outlet.

11. The biomolecule filter of claim 10, wherein the second flow path comprises:
    a second flow path groove comprising a plurality of guide grooves extending side by side at mutually spaced intervals to guide the biomolecules coming out from said second surface of the membrane structure; a collecting groove configured to collect the biomolecules guided and moved by the plurality of guide grooves and to deliver the biomolecules guided and moved by the plurality of guide grooves to the second outlet; and
    an inner diaphragm disposed around the second flow path groove and configured to prevent a leakage of biomolecules.

12. The biomolecule filter of claim 10, wherein the second housing further comprises:
    a second adhesive part comprising an adhesive adhered to the support part of the membrane structure; and
    a second vent hole configured to enable the second adhesive part to communicate with an exterior of the second housing.

\* \* \* \* \*